(12) United States Patent
Henry et al.

(10) Patent No.: US 8,083,162 B2
(45) Date of Patent: Dec. 27, 2011

(54) METHOD FOR MICRO-SIZING ORGANIC, INORGANIC AND ENGINEERED COMPOUNDS

(75) Inventors: William S. Henry, Moorestown, NJ (US); Edwin B. Fay, Cinnaminson, NJ (US); Ronald R. Warnecke, Idaho Falls, ID (US); Gary L. Palmer, Shelley, ID (US)

(73) Assignees: LiquaJet L.L.C., Moorestown, NJ (US); Nitrocision L.L.C., Idaho Falls, ID (US)

( * ) Notice: Subject to any disclaimer, the term of this patent is extended or adjusted under 35 U.S.C. 154(b) by 166 days.

(21) Appl. No.: 12/171,176

(22) Filed: Jul. 10, 2008

(65) Prior Publication Data

US 2009/0050718 A1 Feb. 26, 2009

Related U.S. Application Data

(60) Provisional application No. 60/966,103, filed on Aug. 23, 2007.

(51) Int. Cl.
*B02C 19/06* (2006.01)

(52) U.S. Cl. ........................ 241/5; 241/DIG. 37

(58) Field of Classification Search ............... 241/5, 18, 241/23, 39, DIG. 37
See application file for complete search history.

(56) References Cited

U.S. PATENT DOCUMENTS

| | | | |
|---|---|---|---|
| 3,937,405 A | 2/1976 | Stephanoff | |
| 4,863,106 A * | 9/1989 | Perkel | 241/5 |
| 4,930,707 A | 6/1990 | Oshiro et al. | |
| 5,195,695 A | 3/1993 | Ondush et al. | |
| 5,203,511 A | 4/1993 | Ondush et al. | |
| 5,340,776 A | 8/1994 | Paschke et al. | |
| 5,435,496 A | 7/1995 | Kanda et al. | |
| 5,456,629 A | 10/1995 | Bingham | |
| 5,733,174 A | 3/1998 | Bingham et al. | |
| 5,775,603 A | 7/1998 | Kohler et al. | |
| 5,780,806 A | 7/1998 | Ferguson et al. | |
| 5,934,575 A | 8/1999 | Ohnishi et al. | |
| 6,426,136 B1 | 7/2002 | Rouse et al. | |
| 6,428,815 B1 | 8/2002 | Costantino et al. | |
| 6,699,963 B2 | 3/2004 | Noda et al. | |
| 6,715,705 B2 | 4/2004 | Rowley, Jr. | |
| 6,894,088 B2 | 5/2005 | Motier et al. | |
| 6,991,189 B2 | 1/2006 | Hahn et al. | |
| 7,361,209 B1 | 4/2008 | Durham et al. | |
| 7,621,473 B2 * | 11/2009 | Capelle, Jr. | 241/5 |
| 2004/0139624 A1 | 7/2004 | Chickering, III et al. | |
| 2005/0268425 A1 | 12/2005 | Clemons, Sr. | |
| 2006/0049274 A1 | 3/2006 | Hume et al. | |
| 2006/0053165 A1 | 3/2006 | Hume et al. | |
| 2006/0276566 A1 | 12/2006 | Mathew et al. | |
| 2009/0001201 A1 * | 1/2009 | Brantley et al. | 241/5 |
| 2010/0025506 A1 * | 2/2010 | Capelle, Jr. | 241/5 |

FOREIGN PATENT DOCUMENTS

| | | |
|---|---|---|
| CN | 1240162 A | 1/2000 |
| EP | 1 135 659 B1 | 5/2006 |
| GB | 2 318 749 A | 5/1998 |
| WO | WO 2004/052567 A2 | 6/2004 |

* cited by examiner

*Primary Examiner* — Faye Francis
(74) *Attorney, Agent, or Firm* — Flaster/Greenberg, P.C.

(57) ABSTRACT

A method and system are provided herein for forming microparticles from plastic and elastomeric materials that cannot be reduced in size by conventional methods. The system includes a high-pressure liquid nitrogen energy source, a feeder for providing a preferred constant and uninterrupted feed to a mill, a preferred integral injection device to meter the feed into a chamber for milling and/or classification, and a preferred exhaust system for collection of the milled product.

20 Claims, 5 Drawing Sheets

US 8,083,162 B2

METHOD FOR MICRO-SIZING ORGANIC, INORGANIC AND ENGINEERED COMPOUNDS

CROSS-REFERENCE TO RELATED APPLICATIONS

This application claims the benefit of priority under 35 U.S.C. §119(e) of U.S. Provisional Patent Application No. 60/966,103, filed Aug. 23, 2007, the entire disclosure of which is incorporated herein by reference.

BACKGROUND OF THE INVENTION

Microparticles and small particles may be formed using existing jet milling techniques. Such systems, like the Micron-Master™ operated by Jet Pulverizer Co. of Moorestown, N.J. are capable of making friable or certain crystalline materials into small particles using impact methods. Most conventional jet mills operate by injecting fluidized particles into a grinding chamber. The particles are picked up and accelerated, entrained and bombarded against themselves by jets of expanding compressed air or gases entering tangentially to the chamber. Particles are classified to a very narrow particle size distribution by action of centrifugal forces on the particles and drag forces of the gas leaving the mill.

Organic, inorganic and engineered compounds and materials typically fall into three primary categories: (1) friable and crystalline; (2) technically brittle, but extremely tough; and (3) pliable or resilient (which covers many polymeric and elastomeric materials). Friable or crystalline materials can usually be ground with typical jet or mechanical technologies. Tough materials often cannot be ground satisfactorily due to energy limitations that existing impact technologies can apply to these particles. Particle reduction of pliable and resilient materials, like plastics and elastomers, has been limited to mechanical technologies with average particle sizes ranging from about 50-500 microns, with results being dependent on the glass transition temperature ($T_g$) of the material and the ability to make some materials brittle and finer using the help of cryogenics using liquid nitrogen.

BRIEF SUMMARY OF THE INVENTION

Based on the foregoing Background, there is a need in the art for a method for making particles of tough, plastic and elastomeric materials, as well as other difficult-to-mill materials, in particle sizes that are finer than existing technologies are able to produce.

The present method technology is not dependent on existing impact methods used in jet and mechanical milling nor is it dependent on glass transition temperatures. This new technology incorporates an ultra high-pressure (e.g., about 45,000 to about 55,000 psig) stream of liquid nitrogen, which cuts or slices the particles numerous times while taking advantage of the geometry of the vortex action in the modified jet mill to circulate and classify. The result is an average particle size of about 10 to about 40 microns. Negative $T_g$ materials do not have to be made brittle with cryogenics, and positive $T_g$ materials, which cannot be made brittle at lower temperatures, can be reduced into the lower micron sizes. One particle can be split by the method herein into about one million particles and surface area increased by about 10,000 percent. For example, methyl acrylate can be micro-sized to about 13 microns, polyamides (nylons) to about 42 microns, and polylactide resins to about 34 microns.

Described herein is a method for milling a material, including introducing a material to be milled into a milling chamber, wherein the milling chamber has an outer wall, and an inner wall defining a milling area and the material is fed into the milling area; introducing a stream of nitrogen to the milling area through an inlet feed jet, wherein the nitrogen stream is fed at a pressure of about 45,000 psi (310 MPa) to about 55,000 psi (379 MPa); contacting the material in the milling area with the stream of nitrogen so as to form milled microparticles of the material; and removing the milled microparticles from the milling area.

In one embodiment, the material to be milled is selected from the group consisting of an elastomeric material, a plastic material and combinations thereof. The material may also have a positive glass transition temperature.

The method may also include introducing the material into the milling area through a pressurizing inlet. The pressurizing inlet may be a venturi nozzle and the material enters at a pressure of at least 85 psig. The material may enter the pressurizing inlet with a pressurized gas. The pressurized gas may include nitrogen. In another embodiment, the milling chamber includes four inlet gas jets and the method further includes feeding four streams of nitrogen into the milling area.

The method may include a stream of nitrogen entering the milling area at a location of the inlet feed jet at an angle to the inner wall of the milling chamber, which preferably has a circular cross-sectional configuration, and as a tangent to a circle concentric with the inner wall of the milling chamber, wherein the concentric circle includes about 60% to about 85% of a cross-sectional area of the chamber, as measured longitudinally across the chamber. In one embodiment, the circle includes about 70% to about 75% of the cross-sectional area of the chamber.

In a further embodiment, microparticles are formed having an average particle size of about 10 to about 40 microns, and preferably of about 20 microns.

The method may also include classification and/or filtering the milled microparticles removed from the chamber.

In another embodiment, the stream of nitrogen is a stream of high-pressure liquid nitrogen and the method further includes introducing the high-pressure liquid nitrogen at a pressure of about 45,000 psig (310 MPa) to about 50,000 psig (344 MPa) and a temperature of about −140° C. to about −151° C.

Also described herein is a system for forming microparticles from a material to be milled. The system includes a high pressure nitrogen source having an outlet; a feeder for providing a feed of the material to be milled; and a milling chamber which comprises: (i) an outer wall; (ii) an inner wall defining a milling area; (iii) an inlet gas jet capable of providing flow between the outlet of the high pressure nitrogen source and the milling area; (iv) a feed inlet capable of providing flow between the feeder and the milling area to allow a material to be milled to be introduced into the milling area; and (v) an outlet through which milled microparticles are removed from the milling area.

In one embodiment, the outlet of the high-pressure nitrogen source in the system is further able to provide flow through a chiller for chilling high-pressure nitrogen prior to entering the milling area through the inlet gas jet.

In another embodiment, the milling chamber includes at least four inlet gas jets. The inner wall of the milling chamber in this embodiment is circular in cross-sectional configuration and the stream of nitrogen that enters the chamber is at an angle with the inner wall of the chamber and enters as a tangent to a circle concentric with the inner wall of the chamber, wherein the concentric circle includes about 60% to about 85% of a cross-sectional area of the chamber, as measured longitudinally across the chamber. In one embodiment, the circle includes about 70% to about 75% of the cross-sectional area of the chamber.

The outlet of the milling chamber in the system may also be capable of providing flow to a filtering device and collector.

A milling chamber is also described herein for forming milled microparticles, including: (i) an outer wall, (ii) an inner wall defining a milling area, (iii) an inlet gas jet configured for introducing a stream of high pressure nitrogen into the milling area, (iv) a feed inlet capable of providing a material to be milled to the milling area and (v) an outlet through which milled microparticles may be removed from the milling area.

In one embodiment, the milling chamber preferably has a circle concentric with the inner wall of the chamber. The inner wall of the chamber defines an angle with the stream of nitrogen that enters the chamber tangent to the concentric circle. The concentric circle includes about 60% to about 85% of the cross-sectional area of the chamber, as measured longitudinally across the chamber. In one embodiment, the circle includes about 70% to about 75% of the cross-sectional area of the chamber.

BRIEF DESCRIPTION OF THE SEVERAL VIEWS OF THE DRAWING(S)

The foregoing summary, as well as the following detailed description of preferred embodiments of the invention, will be better understood when read in conjunction with the appended drawings. For the purpose of illustrating the invention, there is shown in the drawings embodiments that are presently preferred. It should be understood, however, that the invention is not limited to the precise arrangements and instrumentalities shown. In the drawings.

DETAILED DESCRIPTION OF THE INVENTION

Described herein are a method for milling a material, a system for forming microparticles and a milling chamber. A method, system and new milling chamber are provided which are able to provide microparticles of an average particle size of about 10 to about 40 microns and as small as about 20 microns. The method allows for formation of particles in smaller sizes that were hitherto unable to be formed, and provides a method for milling particles that did not previously lend themselves to milling due to the glass transition temperature of the material.

Figure 1:
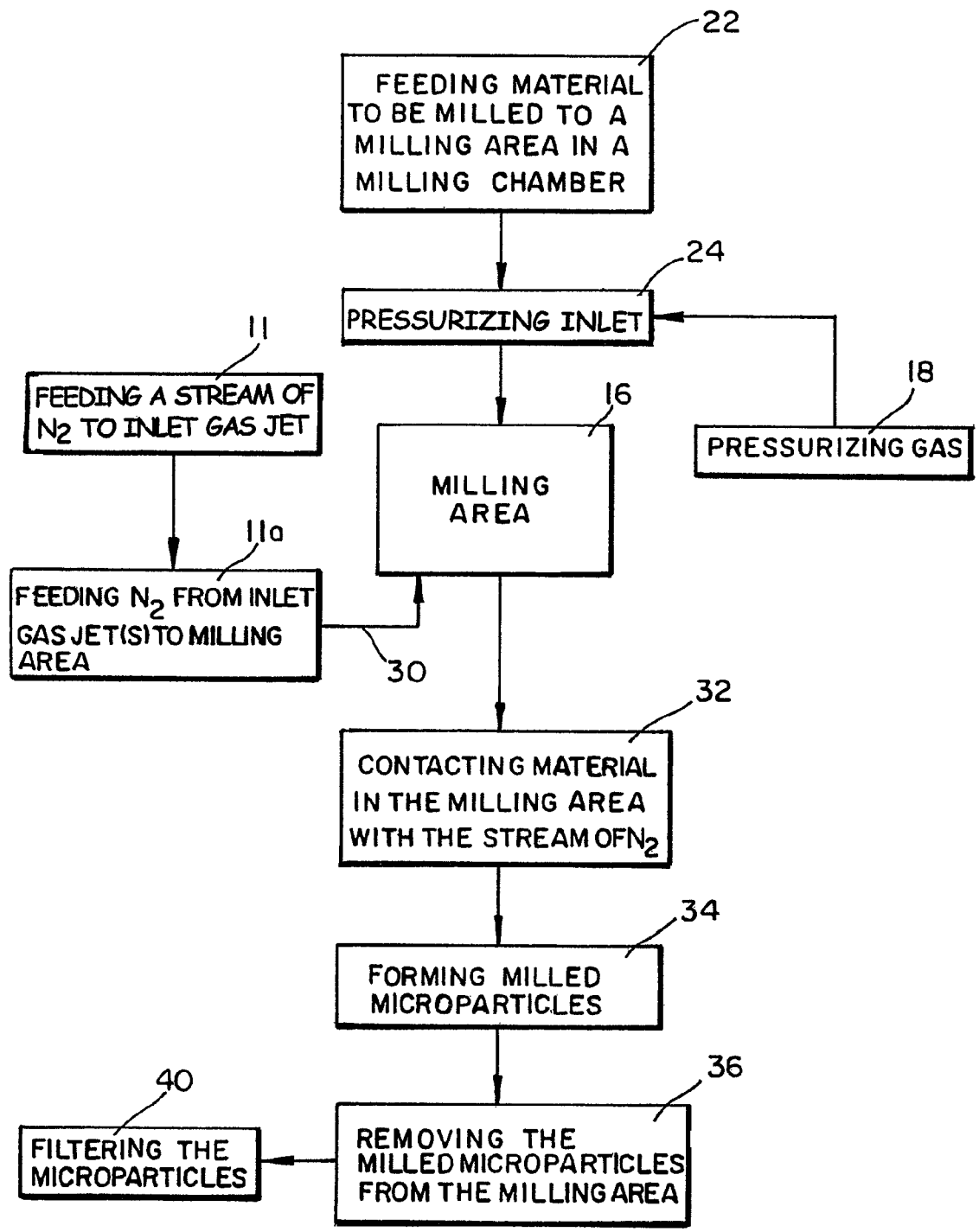
FIG. 1 is a block diagram of the steps of a method for milling a material according to an embodiment of the invention.

As shown in FIG. 1, in the block flow representation of a preferred embodiment of the method for forming microparticles, the method includes a step 22 of introducing a material to be milled into a milling chamber, such as by feeding, and particularly through a pressurizing inlet with a pressurizing gas as in step 24 into the milling area of a milling chamber. As used herein, "introducing" of materials is meant in the broadest sense and can include, for example, placing, inserting, feeding, or otherwise inserting materials into the chamber.

It will be understood, based on this disclosure, that the method of milling may be used on a wide variety of materials, with a particular focus on being able to mill things into small, microparticle sizes on materials that have previously not been susceptible to conventional milling techniques. It is particularly useful for materials that are difficult to break or fracture using conventional milling, including particles that do not benefit from, for example, cryogenic pretreatment to embrittle the material to assist in milling. Thus, materials such as polymers that have negative glass transition temperatures can typically be made brittle through a liquid cryogenic pre-cooling to facilitate milling. The present method can also be used to grind materials, such as polymers, that have a positive glass transition temperature, where pretreatment through liquid cooling has not been shown to have an effect and which other existing milling technologies have not been able to mill. Thus, novel microparticle-sized materials can be provided by the method for use, for example, in the chemical, pharmaceutical, food and cosmetics industries.

The materials that can be milled may include various materials that can be milled using high-pressure liquid nitrogen, including, but not limited to, various polymeric materials such as plastics and elastomers and combinations thereof. Exemplary materials that can be milled using the method herein include various polymers, such as, for example, silicones, polyolefins, polyvinyls, polyesters, polyacrylates, polyamides, polycarbonates, polybutadienes, polystyrenes, polyimides, polyethers, polyetheramides, polyetherimides, polyarylenes, polyarylene ethers, polyurethanes, polyester polyols, polyether polyols, fluoropolymers, perfluoropolymers, superabsorbent polymers, polyacrylonitriles, poly (acrylonitrile-butadiene-styrenes) polyvinylpyrrolidone, epoxy polymers, and copolymers, mixtures, graft polymers, alloys and blends of the various above-noted polymers (and monomers forming the various polymers) thereof. In addition, other exemplary materials that can be milled according to the method herein include waxes, molecular sieves, pharmaceutical compounds, fats, starches, carbohydrates, polysaccharides, surfactants, and epoxies.

Elastomers may also be milled including polyolefinic rubbers (ethylene-propylene-diene rubber (EPDM), ethylene, propylene rubber (EPR), etc.), polyurethane rubbers, polystyrene rubbers, polyamide rubbers, polybutadiene rubber, neoprene, polychloroprene rubber, natural rubber, fluoroelastomers, perfluoroelastomers, and other vulcanized and cross-linked polymers providing elastomeric (at least partial recovery upon stretching) properties, as well as copolymers, blends, mixtures and variations thereof.

Figure 3:
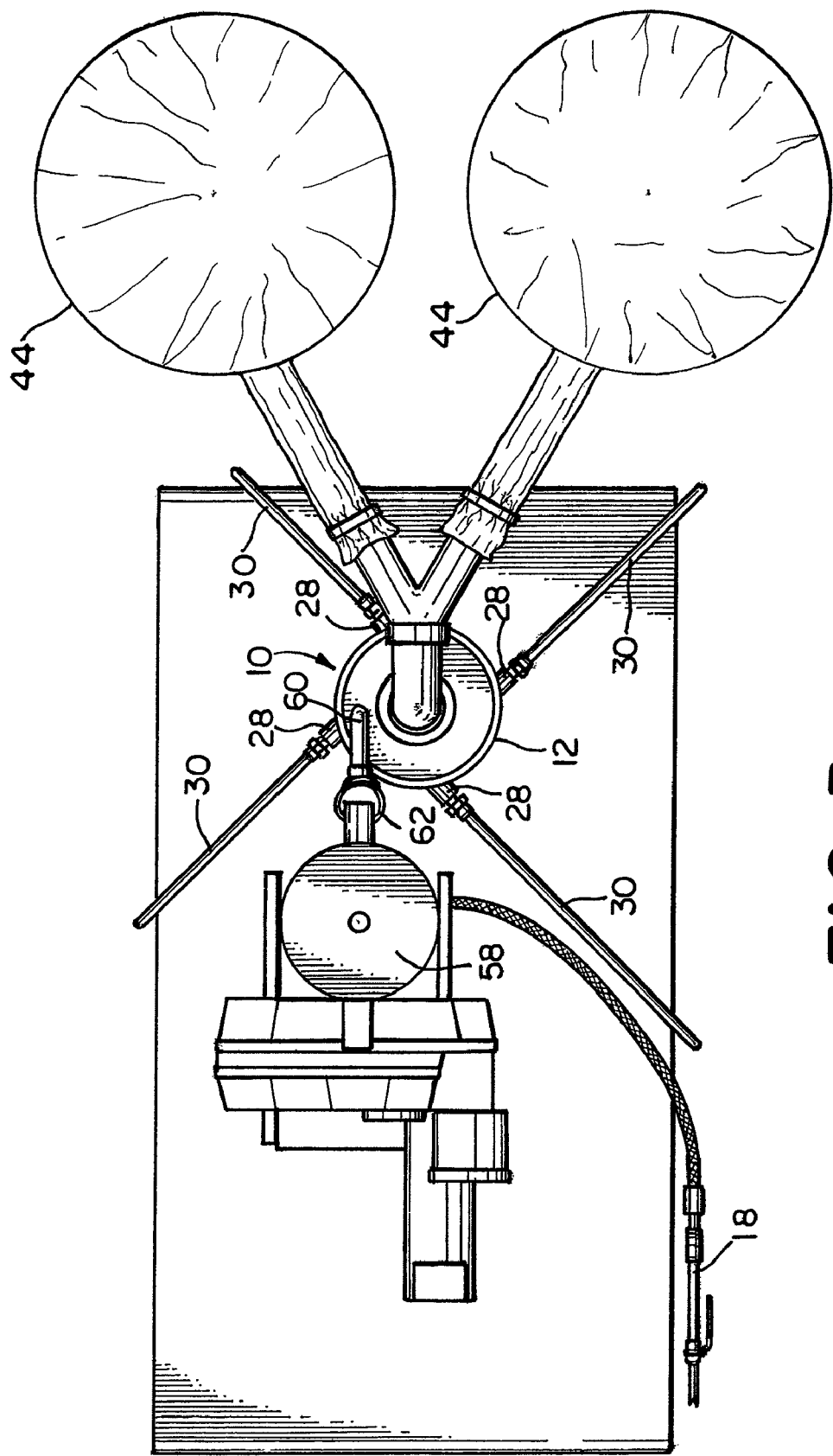
FIG. 3 is a top elevational view of a milling chamber in a system for forming microparticles according to an embodiment of the invention.
Figure 4:
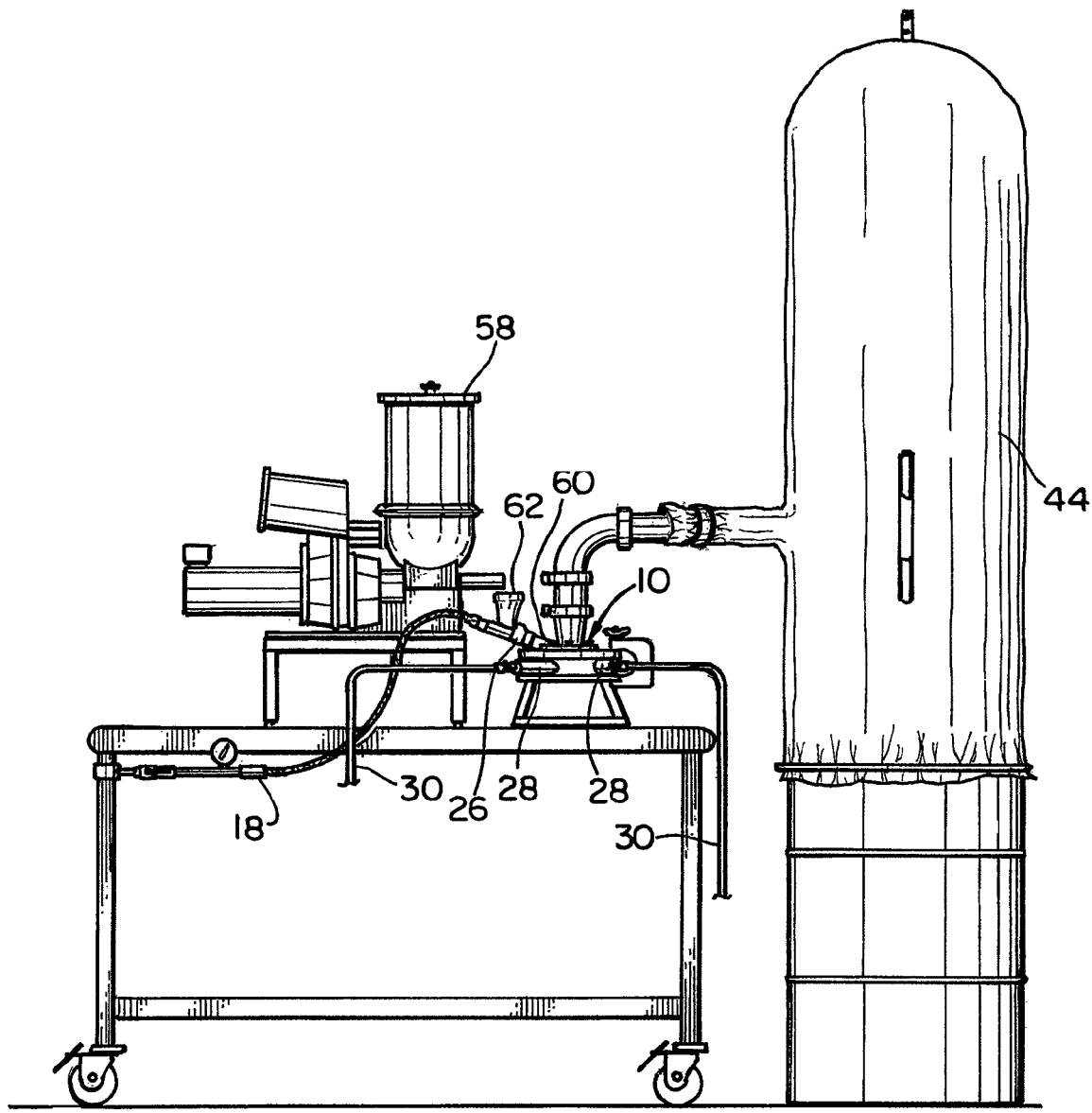
FIG. 4 is a side elevational view of the milling chamber the system for forming microparticles according to the embodiment shown in FIG. 3.
Figure 5:
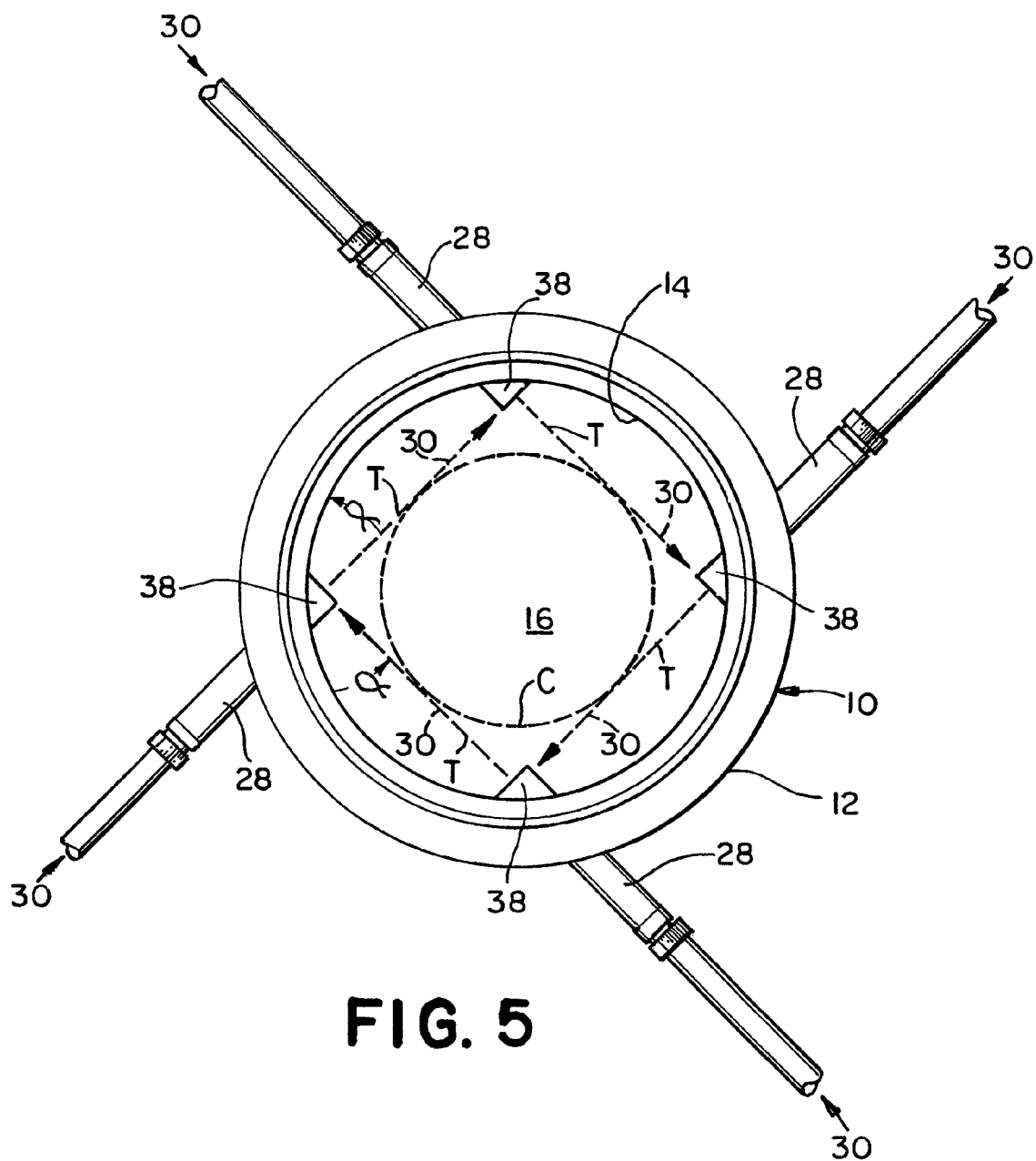
FIG. 5 is a top elevational view of an open milling chamber according to an embodiment of the invention showing direction of high-pressure nitrogen flow.

The milling chamber is shown in FIG. 3-5. As best shown in FIG. 5, the milling chamber has an outer wall 12, and an inner wall 14 defining a milling area 16. The material to be milled is fed into the milling area from a source 20 of the material to be milled in a step 22 of the method herein.

In one embodiment, the material to be milled may already be in small sizes, e.g., particles, pellets and the like. The nature of the material shape is not limited, however, in one embodiment, the method may be practiced generally with a reasonably uniform (e.g., commercial) feedstock. Experimental feedstock or variable size feedstock is also contemplated in this disclosure. The feed material may be of varied sizes and inlet feed orifice size chosen accordingly. In one preferred embodiment, the feed material is in a unit on the order of magnitude of about 0.0001 cm to an order of about 1 cm as measured in largest diameter. In yet a further embodiment, the feed material is about 0.001 to about 0.5 cm in the largest dimension. It should be understood by one of ordinary skill in the art, that one can vary the feed inlet orifice to accommodate varying size particles. In one embodiment herein, the average particle size is from about 30% to about 60%, and in yet a further embodiment, it is about 40% to 50% of the inner diameter of the orifice of the inlet for the feed material into the milling chamber to provide smooth flow of the material and a relatively constant feed rate. The disclosure should not be deemed limited however, but the relation of orifice size and feed particle size in view of the general concept described herein.

The material may be introduced in varying ways into the milling area of the milling chamber. The materials may be introduced by plug flow or under pressure, it may also, if desired be heated or cooled prior to pretreatment for differing effects, although preheating or precooling are not necessary to achieve the benefits of the method. In one particular embodiment, the material is injected into the chamber under pressure using a pressurized gas 18, which may be dry of moisture, such as pressurized nitrogen. However, other gasses may work and the pressure may be varied from slight to moderate to high depending on variations in the process. In a particular, preferred embodiment, the material may be fed to the milling area of the chamber through a high pressure valve as a pressurizing inlet as in step 24, such as a venturi 26 which combines the material particles to be fed and a pressurized gas to inject the material into the chamber under pressure. However, other pressurizing nozzles or valves may also be used as are known in the art or to be developed, such as injectors, pusher nozzles, or other gas feed jets, including dual flow turbulent nozzles.

In a particular embodiment herein, the material feed gas is dry so as to not introduce moisture into the milling chamber that may freeze and plug the mill due to the use of high-pressure liquid nitrogen as described below. As a result, in such embodiment it is recommended to use dry nitrogen pressurized feed gas. If a pressurized gas is used to introduce the feed material to be milled, it may be fed at varying pressures depending on the feed rate and pressure desired for introducing the feed material. In one particular embodiment the material enters at a pressure of at least about 85 psig to about 120 psig, but higher pressures are also within the scope of the disclosure.

Figure 2:
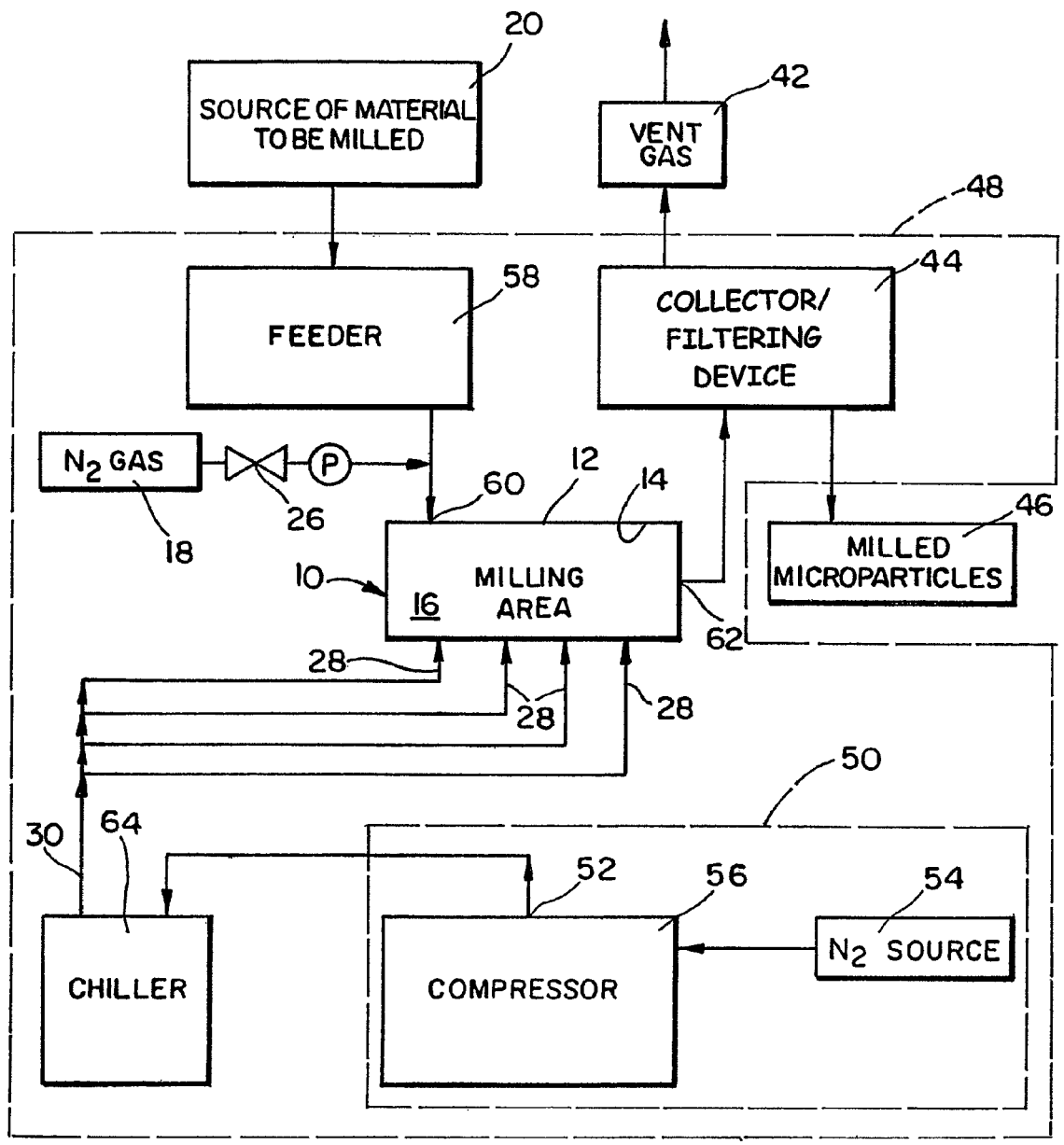
FIG. 2 is a block diagram of a system for forming microparticles according to an embodiment of the invention.

The method also includes as in FIGS. 1 and 2, in a step 11, introducing a stream of nitrogen from one or more inlet gas jets as in step 11a into a milling area 16 of a milling chamber, generally referred to herein as 10 as in FIG. 2. The stream of nitrogen 30 may enter the milling area 16 of the milling chamber 10 through an inlet gas jet 28, wherein the nitrogen stream 30 is fed at a very high pressure of about 45,000 psig (310 MPa) to about 55,000 psig (379 MPa). The stream of nitrogen 30 is most preferably at a very high pressure, and is most preferably a stream of high pressure liquid nitrogen at a pressure of about 45,000 psig (310 MPa) to about 55,000 psig (379 MPa) and a temperature of about −140° C. to about −151° C., with a preferred pressure approaching 55,000 psig (379 MPa) and a temperature at about 146° C.

In one particular embodiment herein, the milling chamber includes more than one inlet gas jets and more than one corresponding stream of nitrogen in order to provide good milling action. In a more particular embodiment, there are four such inlet gas jets and four streams of nitrogen. However other configurations and varying numbers of jets may be used within the broader scope of the disclosure. The inlet gas jets are preferably equidistantly spaced around the wall of the milling chamber such that the stream(s) of nitrogen strike incoming particles at varying locations throughout the chamber.

In one particular embodiment, as shown in FIG. 5, a concentric circle C is shown, which is concentric with the inner wall, which also has a circular cross-sectional configuration as shown. The circle C has various tangents T which also correspond to the streams of nitrogen 30. For example, a stream of nitrogen 30 may be fed at a location 38 and at an angle α. The angle α is defined by the inner wall and the stream of gas that enters the chamber so as to form tangent T with the concentric circle C. In this embodiment, the concentric circle C circumscribes about 60% to about 85% of the cross-sectional area of the chamber, as measured longitudinally across the chamber, and preferably about 70% to about 75% of the cross-sectional area of the chamber. The gas jet introduces gas into the chamber at the situs of the inner wall 14 of the milling chamber, which inner wall defines the milling area 16.

After the material to be milled and the stream of nitrogen enter the milling area of the milling chamber, the material is contacted with the stream of nitrogen as in step 32 as in FIG. 1 so as to form milled microparticles of the material as in step 34. The stream of nitrogen is at a sufficiently high pressure that it is able to cut the feed material particles into microparticles. As used herein "cutting" of the particles includes actions such as direct cutting, slicing, dicing and the like to separate the particle by a cutting action. In an embodiment using high-pressure liquid nitrogen as a cutting agent, the particles are cut almost as though they were laser cut as they pass through the streams of nitrogen. The disclosure herein provides a unique method of micro-sizing particles, including particles of materials not previously susceptible to formation at such a micro-sized level using conventional grinding or impact bombardment techniques available with conventional milling.

After the microparticles are formed, they are removed from the milling area as in step 36 of FIG. 1. In particularly preferred embodiments, the microparticles as formed have an average particle size, as measured in the longest dimension of the particle, of about 10 to about 40 microns, and most particularly of about 20 microns or less. This level of microparticulation allows for splitting of some single particles, for example, into on the order of one million particles and for an increase in available particle surface area of about 10,000 percent. The method and system described herein provide for size reduction of tough or hard particles difficult to break or fracture using conventional milling methods as well as for cutting of particles that are not otherwise benefited by cryogenic pretreatments preceding conventional milling. Materials with both negative and positive glass transition temperatures may be cut into microparticles using the method, system and milling chamber described herein.

In one further, particular embodiment, the method further includes collecting the milled microparticles removed from the chamber along with the spent nitrogen gas and venting the gas 42 as in FIG. 2, and filtering and collecting the microparticles in a suitable filtration/collection device 44 as a product 46 of the method as in step 40.

A system is also described herein for forming microparticles from a material to be milled, wherein the system is shown in schematic form as system 48 in FIG. 2. The system includes a high-pressure nitrogen source 50, preferably a source of high-pressure liquid nitrogen, having an outlet 52. The high pressure nitrogen source should include a nitrogen source 54 and compressor 56 capable of delivering nitrogen at pressures of about 45,000 psig (310 MPa) to about 55,000 psig (379 MPa), and preferably providing a stream of high pressure liquid nitrogen at a pressure of about 45,000 psig (310 MPa) to about 55,000 psig (379 MPa) and a temperature of about −140° C. to about −151° C., with a preferred temperature at about 146° C. In a preferred embodiment, the high pressure liquid nitrogen enters the milling area and converts to gas at an expansion ratio of about 700:1 which violent expansion allows for circulation of particles and centrifugal classification. Larger particles are thrown toward the outside of the milling area, while smaller particles are dragged to the center as the gas feed escapes carrying a mixture of smaller particles and venting gas from the milling area. A suitable high-pressure nitrogen source includes high-pressure liquid nitrogen as delivered through a high-pressure liquid nitrogen compressor capable of achieving the above-noted desired feed pressures and temperatures. Suitable compressors are described in U.S. Patent Publications Nos. US 2006-0053165 A1 and US 2006-0049274 A1, each of which are incorporated herein by reference in relevant part.

The system 48 also further includes a feeder 58 for providing a feed of the material to be milled. The feeder 58 introduces the material to be milled into a milling chamber, such as milling chamber 10, which includes an outer wall 12, an inner wall 14 defining a milling area 16 as shown in FIG. 5. The milling chamber in the system 48 also includes one or more inlet gas jet(s) 28 capable of providing flow between the outlet 52 of the high-pressure nitrogen source 50 and the milling area 16, wherein the inlet gas jet(s) 28 may be in flow communication directly or indirectly between outlet 52 of the high-pressure nitrogen source 50 and the milling area 16. In one embodiment herein, the outlet 52 of the high-pressure nitrogen source 50 is further able to provide flow through a chiller 64 for further chilling high-pressure liquid nitrogen prior to entering the milling area 16 through the inlet gas jet(s) 28. In one embodiment, the outlet 52 of the high-pressure nitrogen source 50 is able to provide direct or indirect flow communication to the chiller 64. Milling chambers can vary in size with respect to the milling area 16. Applicants have carried out the process using both 4 inch (10.16 cm) and 8 inch (20.32 cm) jet pulverizer Micron-Master™ Jet Pulverizer™ jet mills, from Jet Pulverizer Co., Moorestown, N.J., fitted with the high pressure liquid nitrogen inlet gas jets and connected to a high pressure liquid nitrogen source. However, other jet mills of varying size may be used within the scope of the disclosure.

In a particularly preferred embodiment herein, the milling chamber 10 has at least four inlet gas jets 28, although this may be varied as noted above. The selection, placement and number of inlet gas jets 28 may be varied, depending on the milling and cutting effect desired as well as the size of the milling chamber. Larger chambers can accommodate more and varied arrangements of inlet gas jets 28, and one skilled in the art will understand based on this disclosure that the milling chamber may be varied to include different cutting and microparticulation effects. The inlet gas jets 28 each can be varied as well in inlet size based on the desired liquid nitrogen expansion effect and the size of the milling chamber's milling area 16. The jet size (inlet) may be varied, and is preferably about 0.001 inch (0.00254 cm) to about 0.1 inch (0.254 cm). The inlets may be formed using microdrilling or boring of a crystal, or similar hard material, which may be mounted within a holder capable of sustaining it in place, such as through threads, snap-fit, inset, locking and/or mating connectors and the like. This high pressure liquid nitrogen feed into such a small inlet, create "supply whips" which enable gas expansion desired to create from about 50 to about 1000 standard cubic feet per minute or more and should be adjusted to be workable in the size of milling area. The milling area must be able to accommodate the gas pressure expansion.

The milling chamber also has a feed inlet 60 that is capable of providing flow between the feeder 58 and the milling area 16 so as to provide material to be milled to the milling area 16. In one embodiment, the feed inlet 60 provides flow communication directly or indirectly between the feeder 58 and the milling area 16. Introducing, such as by feeding, of raw material to the process should be reasonably constant for optimal operation. A vibrating trough feeder or similar feeding mechanism works well for pelletized feed. For introducing, such as by feeding, powder material, augers or screw conveyors may be used. The feeder is not limited, but developing a steady and accurate feed rate is most preferred.

The milling chamber has an outlet 62 through which milled microparticles 46 may be removed from the milling area 16. In one embodiment herein, the outlet 62 of the milling chamber 10 may be capable of providing flow of milled material to a filtering device and collector 44 as shown in FIG. 2, which may include a baghouse dust collector or single or multiple collection bags and receiving chambers as shown in FIGS. 3 and 4, where two such bags and chambers are provided. Such flow may be through direct or indirect flow communication between the outlet 62 of the milling chamber and the filtering device and collector 44.

A milling chamber is provided herein for forming milled microparticles, having an outer wall 12 and an inner wall 14 that defines a milling area 16. The chamber includes at least one inlet gas jet 28 configured to introduce a stream of high-pressure nitrogen 30 into the milling area 16. The chamber further includes a feed inlet 60 capable of providing a material to be milled to the milling area 16, wherein the material to be milled is from a source 20 of such material. The feed inlet 60 may provide direct or indirect flow communication between the material to be milled and the milling area 16. The milling chamber further has an outlet 62 through which milled microparticles 46 may be removed from the milling area 16. In a particular embodiment herein, ground product may be discharged into, for example, a cotton filter bag having a filtration area. The ratio of air to cloth based on the filtration area is preferably from about 2:1 to about 7:1, and preferably about 3:1.

In a particular embodiment as noted elsewhere herein, the inner wall 14 of the chamber 10 has the inlet gas jet 28 at a location 38. The inlet gas jet(s) are configured in this embodiment so as to introduce a stream of nitrogen 30 into the milling area 16 at an angle α defined by the inner wall and the stream of nitrogen which enters the chamber so as to form tangent T to concentric circle C, which concentric circle C is concentric with the inner wall and has various tangents T. The stream of nitrogen 30 is preferably fed a location 38. The concentric circle C in this embodiment circumscribes about 60% to about 85% of the cross-sectional area of the chamber, as measured longitudinally across the chamber, and in a more particularly preferred embodiment circumscribes about 70% to about 75% of the cross-sectional area of the chamber.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as described herein.

We claim:

1. A method for milling a material, comprising
introducing a material to be milled into a milling chamber, wherein the milling chamber has an outer wall, and an inner wall defining a milling area and the material is fed into the milling area;
introducing a stream of nitrogen to the milling area through an inlet feed jet, wherein the nitrogen stream is fed at a pressure of about 45,000 psi (310 MPa) to about 55,000 psi (379 MPa);
cutting the material in the milling area with the stream of nitrogen so as to form milled microparticles of the material; and
removing the milled microparticles from the milling area.

2. The method according to claim 1, wherein the material to be milled is selected from the group consisting of an elastomeric material, a plastic material and combinations thereof.

3. The method according to claim 1, wherein the material has a positive glass transition temperature.

4. The method according to claim 1, further comprising introducing the material by feeding the material into the milling area through a pressurizing inlet.

5. The method according to claim 4, wherein the pressurizing inlet is a venturi nozzle and the material enters at a pressure of at least about 85 psig.

6. The method according to claim 4, wherein the material enters the pressurizing inlet with a pressurized gas.

7. The method according to claim 6, wherein the pressurized gas comprises nitrogen.

8. The method according to claim 1, wherein the milling chamber comprises four inlet gas jets and the method further comprises feeding four streams of nitrogen into the milling area.

9. The method according to claim 1, wherein the milling chamber has a circular cross-sectional configuration and the stream of nitrogen enters the milling area at a location of the inlet feed jet at an angle to the inner wall of the chamber and as a tangent to a circle concentric with the inner wall of the milling chamber, wherein the concentric circle comprises about 60% to about 85% of a cross-sectional area of the chamber, as measured longitudinally across the chamber.

10. The method according to claim 9, wherein the concentric circle comprises about 70% to about 75% of the cross-sectional area of the chamber.

11. The method according to claim 1, wherein the milled microparticles have an average particle size of about 10 to about 40 microns.

12. The method according to claim 11, wherein the milled microparticles have an average particle size of about 10 to about 20 microns.

13. The method according to claim 1, further comprising classifying and/or filtering the milled microparticles removed from the chamber.

14. The method according to claim 13, wherein the method further comprises classifying and/or filtering the milled microparticles using a filtering device and collector.

15. The method according to claim 1, wherein the stream of nitrogen is a stream of high-pressure liquid nitrogen and the method further comprises introducing the high-pressure liquid nitrogen at a pressure of about 45,000 psig (310 MPa) to about 50,000 psig (344 MPa) and a temperature of about −140° C. to about −151° C.

16. The method according to claim 15, wherein the method further comprises providing the stream of high-pressure liquid nitrogen from the outlet of a high-pressure nitrogen source having a chiller for chilling the high-pressure nitrogen prior to introducing it to the milling area.

17. A method for milling a material, comprising
introducing a material to be milled into a milling chamber, wherein the milling chamber has an outer wall, and an inner wall defining a milling area and the material is fed into the milling area;
introducing a stream of nitrogen to the milling area through an inlet feed jet, wherein the nitrogen stream is a high-pressure liquid nitrogen stream fed at a pressure of about 45,000 psi (310 MPa) to about 55,000 psi (379 MPa) and at a temperature of about −140° C. to about −151° C.;
cutting the material in the milling area with the stream of nitrogen so as to form milled microparticles of the material; and
removing the milled microparticles from the milling area.

18. The method according to claim 17, wherein the high-pressure liquid nitrogen stream is fed at a pressure of about 45,000 psi (310 MPa) to about 50,000 psig (344 MPa).

19. A method for milling a material, comprising
introducing a material to be milled into a milling chamber, wherein the milling chamber has an outer wall, and an inner wall defining a milling area and the material is fed into the milling area, and wherein the milling chamber has a circular cross-sectional configuration and the stream of nitrogen enters the milling area at a location of the inlet feed jet at an angle to the inner wall of the chamber and as a tangent to a circle concentric with the inner wall of the milling chamber, wherein the concentric circle comprises about 60% to about 85% of a cross-sectional area of the chamber, as measured longitudinally across the chamber;
introducing a stream of nitrogen to the milling area through an inlet feed jet, wherein the nitrogen stream is fed at a pressure of about 45,000 psi (310 MPa) to about 55,000 psi (379 MPa);
cutting the material in the milling area with the stream of nitrogen so as to form milled microparticles of the material; and
removing the milled microparticles from the milling area.

20. The method according to claim 19, wherein the concentric circle comprises about 70% to about 75% of the cross-sectional area of the chamber.

* * * * *